United States Patent [19]

Kritzinger et al.

[11] Patent Number: 5,779,711
[45] Date of Patent: Jul. 14, 1998

[54] CORNEAL FLAP/CAP ELEVATOR

[75] Inventors: Michiel S. Kritzinger, 26 Wexford Avenue, Westcliff, Johannesburg, South Africa; Stephen A. Updegraff, Rapid City, S. Dak.

[73] Assignees: Michiel S. Kritzinger, Johannesburg, South Africa; Stephen D. Updegraff, St. Petersburg, Fla.

[21] Appl. No.: 562,257

[22] Filed: Nov. 22, 1995

Related U.S. Application Data

[60] Provisional application No. 60/001,592 Jul. 27, 1995.

[51] Int. Cl.[6] .................................................. A61F 9/00
[52] U.S. Cl. ............................................. 606/107; 606/167
[58] Field of Search ................................. 606/107, 151, 606/161, 166, 167; 623/4, 5

[56] References Cited

U.S. PATENT DOCUMENTS

| | | |
|---|---|---|
| 3,490,455 | 1/1970 | Illig .................................. 606/107 |
| 3,929,138 | 12/1975 | Curi .................................. 606/167 |
| 4,579,116 | 4/1986 | Catalano ........................... 606/107 |
| 4,643,185 | 2/1987 | Gaba ................................. 606/107 |
| 5,234,436 | 8/1993 | Eaton et al. ...................... 606/107 |
| 5,290,292 | 3/1994 | Householder ...................... 606/107 |
| 5,320,113 | 6/1994 | Tan .................................. 606/107 |

FOREIGN PATENT DOCUMENTS 2247174  2/1992  United Kingdom ............... 606/107

*Primary Examiner*—Robert A. Hafer
*Assistant Examiner*—Justine R. Yu
*Attorney, Agent, or Firm*—Wood,Herron & Evans,L.L.P.

[57] ABSTRACT

An elevating instrument and method for atraumatically lifting a corneal cap or flap during corneal lamellar surgery having a handle and an elevator head at one end of said handle. The head has a leading edge with an inclined top face extending vertically away from said edge and a bottom face for atraumatically engaging the corneal surface. The head is adapted for insertion into a corneal cap or flap incision with said leading edge and inclined top face exposing a corneal edge for lifting the cap or flap.

15 Claims, 1 Drawing Sheet

CORNEAL FLAP/CAP ELEVATOR

RELATED APPLICATIONS

This application is a continuation of Provisional application Ser. No. 60/001,592, filed Jul. 27, 1995, which is incorporated herein in its entirety by reference. This application is also related to copending applications Ser. Nos. 08/561,744, 08/561,541, and 08/652,253, filed on even date herewith and entitled "Corneal Irrigation Cannula and Method of Using", "Corneal Surface Marker and Marking Method for Reducing Irregular Astigmatism During Lamellar (LASIK) Corneal Surgery" and "Method for Reducing Irregular Astigmatism and Debris/Epithelium in the Interface During Lamellar Corneal Flap/Cap Surgery", respectively, which are incorporated herein in their entireties by reference.

BACKGROUND OF THE INVENTION

Lamellar corneal surgery has undergone a steady evolution over the last 50 years. Advancements in the technology, such as automated keratomes and non-freeze, no-suture techniques have markedly improved safety and effectiveness. During the surface ablation craze of the late 80's, Dr. Gholam Peyman, known for his pioneering retina work, realized the utility of preserving all layers of the cornea but taking advantage of the extreme accuracy of the excimer laser. He patented the method for LASIK years ago and studied this technique in his laboratory. He used a YAG laser due to the limited response and acceptance for this technique by the major excimer laser manufacturers. During the years of epikeratoplasty others such as Drs. Lee Nordan and Stephen Slade, as well as Dr. Casimir Swinger were learning and developing freeze myopic keratomileusis for high myopia. By the late 80's, Dr. Slade was one of a hand full of surgeons still performing this demanding technique. When Dr. Luis Ruiz introduced the automated keratome and the in situ non-freeze, nosuture technique to the lamellar bed, Dr. Slade embraced this and has since introduced this technique to thousands of surgeons worldwide. Although a significant advancement, even Dr. Luis Ruiz realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery, most notably Dr. Lucio Buratto of Milan, Italy, and Dr. Ioannis Pallikaris of Greece. The original Buratto technique, however, required cutting a very thick cap and ablating its under surface. Many of these lenticules required suturing, thus required extreme surgical precision and irregular astigmatism rates were quite high. Pallikaris' early work was done on animal models and provided the first histopathology of excimer laser to a lamellar bed. The early Summit excimer laser studies that evaluated the use of lamellar surgery were conducted by Brink et al; however, there was a significant loss of best corrected visual acuity and a wide range of outcomes as new surgeons attempted to perform the original suture dependent Burrato technique.

As surgeons began doing lamellar surgery, they became concerned about the potential for inducing irregular astigmatism as well as introducing debris such as epithelial inclusions in the interface. Fortunately, with the introduction of the automated keratome and non-freeze, non-suture techniques, irregular astigmatism rates are reduced. Debris in the interface, however, continues to be a chronic problem. Many surgeons have resorted to never wearing gloves during lamellar surgery just for that reason. Although infections in lamellar surgery are quite low, when you are the patient that has the infection, percentages do not matter. At present, it is unclear whether or not wearing gloves during lamellar surgery is the standard of care. Thus, we need a way to perform lamellar surgery with gloves safely so as not to introduce debris into the interface.

There is a growing need to introduce lamellar surgery skills to surgeons new to this arena. Surgeons who have been performing ALK will be prepared to make an easy transition to LASIK. Many of the surgeons making the transition from PRK to LASIK appear totally consumed in what type of ablation to use in the bed, when in reality their primary concerns should be a safe keratectomy and repositioning the cap/flap so that there is the least likely chance for debris in the interface or irregular astigmatism. If that can be reproduced, then enhancement is possible and predictability of the ablation for each surgeon will increase with experience.

Recently a very famous clinical researcher in excimer laser technology expressed that his job is now to make surface ablation PRK as good or better than LASIK. Preserving all the layers of the cornea provides quicker visual recovery and the predictability is less dependent upon the ablation characteristics of the laser. Thus, LASIK in its infancy already has a head start over any surface ablation technique. Secondly, PRK retreatment is not predictable, LASIK enhancement is possible. The tremendous amounts of research and development required to create the perfect surface ablation could be better spent in perfecting LASIK for all ranges of refractive errors.

Notwithstanding recent developments in lamellar surgery, techniques and instrumentation are needed to positively impact all lamellar surgeons who have grappled with sight-threatening irregular astigmatism and debris in the interface.

SUMMARY OF THE INVENTION

This invention is directed to an improvement in instrumentation and surgical technique for use when reducing irregular astigmatism and debris/epithelium in the interface during lamellar corneal surgery. More particularly, this invention is directed to an elevating instrument for use in atraumatically lifting a corneal flap or cap during corneal lamellar surgery.

The elevating instrument for use in atraumatically lifting a corneal cap or flap during corneal lamellar surgery comprises a handle and an elevator head at one end of the handle. The elevator head has a leading edge with an inclined top face extending vertically away from the leading edge and a bottom surface for atraumatically engaging the corneal surface. The head is adapted for insertion into a corneal cap or flap incision with the leading edge and inclined top face exposing a corneal edge for lifting the cap or flap.

In a preferred form the elevator head is angularly disposed with respect to the handle to facilitate lifting the cap or flap, for example, at an angle of about 90°. Also, in a preferred form, the elevator head has a convex top face and an arcuate edge which is concave to more readily conform to the incision in the corneal surface.

The head also has a heel and toe section with the handle connected to the heel section and the toe section forming the leading edge having the inclined top face. The bottom surface is concave between the heel and toe sections, whereby only these sections engage the corneal surface in the preferred embodiment. Also, the leading arcuate edge is dull and has rounded corners thereby preventing tear of the corneal edge during lifting.

These and other advantages of the present invention will become more apparent from the drawings and detailed description.

DETAILED DESCRIPTION OF THE INVENTION

Figure 1:
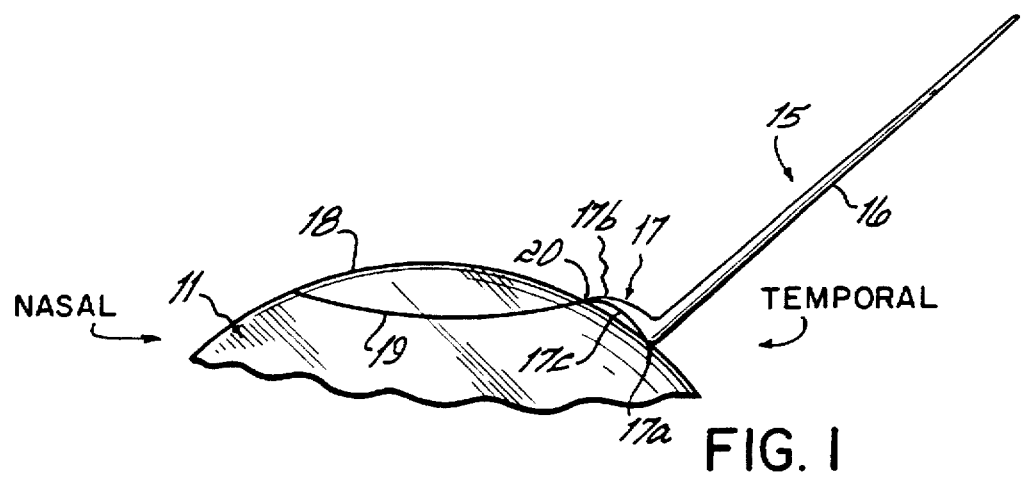
FIG. 1 illustrates a side view of the corneal flap or cap elevating instrument of this invention. The instrument has a handle and a vertically curved blade that engages the corneal surface and keratectomy edge.

I. Overview of the Surgical Procedure (LASIK)

Prior to a lamellar dissection, a marker is used to outline in a specific configuration the anatomical surface of the cornea. Once the lamellar dissection is made and it is appropriate to return the corneal cap/flap, the corneal bed is irrigated with low flow. The flap/cap is returned. Fluid is aspirated from the fornices such that fluid flows from the bed (top of the dome of the eye) out and downward to the fornices. This first step removes debris and epithelium from the interface. Irrigation should start centrally and move peripherally. The second step requires the suction cannula to be placed gently on the edge of the keratectomy to prevent debris/epithelium from wicking back under the flap/cap. With a layer of irrigation fluid in the interface, the corneal flap/cap is then aligned with the preoperative surface marking. If debris continues to be present or the cap is not aligned, the method is repeated.

A. Preoperative ALK or LASIK

1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS should be conducted. As many have noticed for a long time during cataract surgery when meibomian secretions present as a layer in a pool of irrigating solution, a quick irrigation with the I&A with the head tilted will remove this oily film in a large sheet. This is what we believe is happening when they tilt the patient's head and have already done the lid scrubs and irrigate the fornices. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative

1. Draping

This is one of the most important steps. Whatever drape you plan to use, it must retract the eyelashes out of the field and the drape should not restrict the speculum from opening fully so that adequate exposure of the globe can be obtained for suction. We presently use a 10-24 drape made by 3M to accomplish this.

2. Irrigation System

At present, we have been using the roller clamp on the IV bottle to control the flow of the BSS Plus through the irrigation cannula. We have found that it is best if this flow is just adequate to float a cap or flap off the bed without creating distortions, undulations or undue turbulence. This irrigation can also be used to irrigate the globe and cornea prior to surgery.

3. LASIK Marking System

Lamellar corneal surgery has undergone many changes in instrumentation and technique. The most recent advancement is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication, which can be sight threatening of lamellar corneal surgery is irregular astigmatism. To date, corneal surgeons have used subtle and often imperceptible visual cues to reapproximate the flap or corneal tissue. It is apparent that a slight decentration or disorientation of the flap can result in irregular astigmatism. We propose the concept of a corneal surface marker, the Kritzinger-Updegraff (KU) LASIK marker, to improve centration of the procedure and the precise repositioning of the corneal cap or flap. This marker was developed to permit a centered keratectomy which is dependent upon an outer ring on which the surgeon centers the suction ring. The marker also has six radial and two pararadial marks within it. These radial marks vary in width which permits precise repositioning of the cap or flap edges. This prevents micro-decentration seen when the surgeon uses an equally gapped gutter as the cue for alignment. The pararadial marks aide in preventing a reversed free cap.

The marker consists of two concentric rings; one 5 mm in diameter with cross-hair (to aid centering) and 10 mm to 10.5 mm in diameter radiating off the center ring are six radial and two pararadial marks. The width of the superior and inferior radials as well as one temporal pararadial are two times thicker than the other radials. The pararadials at 11:00 and 1:00 are of different width to ensure proper orientation of a free cap and prevent placement of a free cap upside down (epithelial surface down). The concentric rings ensure centration of the mark and subsequent centration of the LASIK suction ring. The different widths of the pararadials and radials permit accurate, anatomic repositioning of the cap or flap with microsurgery. The radiating marks extend beyond the outer ring to provide adequate reference points with the large flaps made with the LASIK suction ring.

4. Centration a. Positioning the Patient's Head

The goal is to have the globe absolutely centered in the patient's socket as the patient fixates on the red fixation beam. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the cross-hairs that are in the optics of the right eye piece. The KU marker is then positioned so that the superior and medial lateral marks of the cross-hair match with those of the marker. Thus, after creating the mark the cross-hairs can be superimposed upon it. If there is not absolute correspondence of the cross-hairs in the mark that is placed on the cornea, the surgeon is then responsible to make a "mental note" of this orientation when ablating the stromal bed and putting the flap back into position. At this point with the Keracor 116 laser, the red and green light must be superimposed prior to placing these marks or the cross-hair will move away from the center of the pupil after these maneuvers have been performed.

b. applying the Suction Ring

It is important to have the circular mark of the KU marker aligned concentrically with the suction ring. This ensures that the flap will be central to the pupil.

c. Ablation

After the keratectomy is performed, the flap is folded back nasally. The peripheral markings of the KU marker are still visible. Thus, these are used as a visual cue to line up the cross-hair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient's head has moved and thus must be oriented back to the position you had initially worked so hard to achieve. Do not play with the joy stick.

d. Added Security Measures

When using the Keracor 116 laser, leave all three lights on; two red lights and one green light. The one red light with a green indicates that as you are lasering you are at the correct level of focus. The other red light follows the actual laser and indicates the orientation of the laser beam whether it is astigmatism or spherical correction. This is an added security measure to ensure that you are lasering the proper axis.

e. Centering Pearl

When you are lasering, turn the light down and ask the patient continuously to look into the red fixation light. This is a cross-check to ensure that the patient is centering on the cross-hair and that the laser treatment is in the center of the pupil. Between each zone of treatment, we recommend either using a spatula or hockey stick to wipe excess fluid from the stromal surface.

f. Addendum to Centration

Eye trackers can be very helpful, however, we feel that these steps in centering the globe are much more fail-safe and ultimately efficient.

5. Suction Rings a. Adjustable Ring

The adjustable suction ring can be used for LASIK, however, this consistently creates a small flap or cap. On average, the diameter is 7.2 mm. For standard ALK cases, we do not recommend routinely trying to use the excimer laser suction ring because the grooves in the sclera that this creates do not match the adjustable suction ring and it can be difficult to center your suction ring for the very critical refractive pass with standard ALK.

b. LASIK Suction Ring

This ring has a larger inside diameter than the adjustable suction ring and it allows the keratome to be exposed to more cornea thus creating keratectomies which are on the average 8.55 mm in diameter. This is the suction ring of choice for LASIK. However, when placing this suction ring on a globe that retropulses fairly freely, it is important to proptose the globe with a speculum so that the suction ring has a firm adherence to the globe prior to initiating suction. Because the outside of the LASIK suction ring is a smaller diameter than the adjustable suction ring, firm pressure on the suction ring handle can retropulse the globe and thus make it difficult to have clearance for the keratome. The adjustable suction ring on the other hand has a large place that will rest on the eyelids and if the globe is proptosed it will be held by the suction of the suction ring and in turn the suction plate will be held upwards by the lids thugs providing easier exposure. This will become less of significance as surgeons gain experience with the fixed LASIK suction ring.

6. Ablation

Remember to center with KU marker cues.

7. Irrigation Aspiration Instrument and Technique

Once the keratectomy is made, a 19 gauge Bishop Harmon anterior chamber irrigating cannula is introduced underneath the flap. As previously mentioned, the irrigation flow should be adjusted so that the cap/flap floats gently above the bed. The goal is to have the patient fixating so that the apex of the globe is in line with the microscope. This will allow the fluid to flow from underneath the cap or flap peripherally and out past the limbus into the fornices. The fornices can be aspirated with a low flow aspiration. This removes epithelial debris and lint from the interface. After approximately 15 to 20 seconds of this form of irrigation, the irrigating cannula can be moved centrally towards the hinge and gently swept back and forth from the hinge and then held centrally again. This allows any epithelium entrapped by the blade at the hinge to be freed and irrigated out. Once the fornices are cleared of fluid, the aspiration cannula can be moved towards the gutter and with a low flow irrigation, the cap can be nudged so that the radial marks are fairly aligned. Once this is achieved, the gutter should be aspirated for 270 degrees, while there is steady irrigation. This again removes debris that could have hung up at the edge of the keratectomy and not run to the fornices. Aspiration of the gutter is continued as the irrigating cannula is gently withdrawn taking note of the approximation of the radial and pararadial marks. We are presently using a curved tying forceps to smooth the flap from the center to the periphery in making sure the radial and pararadial marks are aligned. If alignment is not achieved, the irrigating cannula is once again reintroduced and the aspiration is preformed in the gutter and the cap is allowed to be adjusted on a bed of fluid.

8. Cap/Flap Adherence a. Air blown on the surface of the cornea can be used working from the center of the corneal surface to the periphery for adherence to the cap/flap. This wicks out fluid from the center to the gutter which again improves the removal of debris and epithelial inclusions from the interface. We believe that there is a higher incidence of folds or cracks in Bowman's membrane when air is used. We also believe that using surface air requires one to work very quickly, because the cap will adhere very rapidly, thus it must be well-centered before the air is introduced. Presently, we prefer to use merocel sponges and very carefully use the tip of this to wick the fluid from the gutter and out from underneath the cap/flap. Extreme care must be taken when using the merocel to remove the fluid in that the patient must have solid fixation. If the patient looks into the wech-cel, the edge of the cap or flap will become bunched up and potentially dislodge the perfect orientation we had previously achieved with the irrigation and aspiration maneuver. However, we do find that with approximately three minutes of time the cap or flap is quite adherent by using this maneuver.

b. Adherence Tests (1) Slade Stria Test

By taking a pair of curved tying forceps and gently depressing approximately 1–2 mm away from the keratectomy gutter, one can see folds or stria originating from the point of depression in the cornea up past the gutter and on the surface of the cap or flap. This should be seen for 360 degrees upon depression. If there are no stria two things are occurring, (a) the cap of flap has not adhered to the bed; (b) the cap of flap has possibly folded on itself on the edge and is preventing adherence of the or flap. With the merocel drying technique, we typically place a drop of BSS on the central cornea while drying the gutter. This improves postoperative visual recovery and aids in patient fixation.

(2) Blink Test

Have the patient repeatedly blink his or her eyes following the Slade Stria Test to confirm the adherence of the cap or flap. One must be very cautious when removing the 10-24 drape. We typically remove the drape as we remove the lid speculum and that way the lid speculum retracts the drape away from the globe as we move them simultaneously. Caps and flaps have been dislodged upon removing speculums and more likely when the edge of a sharp drape catches the keratectomy of the cap and either totally dislodges it or disorients it so that irregular astigmatism is present after surgery. On should always check with the blink test after the drape is removed.

II. Corneal Cap/Flap Elevator of the Present Invention

The present invention and its advantages will be better understood from the above outlined stages of the surgical procedure and the following detailed description incorporating references to the accompanying figures. In the various figures, like reference characters are used to designate like parts.

With recent advancement and popularity of LASIK which is outlined in detail above, there has been a growing need to provide a system for accurate re-treatment of these patients. Due to the varied ability and surgeon variation in ablation patterns, under corrections of the patient's refractive error can result. Some surgeons have advocated performing a complete new lamellar keratectomy. However, this has been shown to cause slivering of the cornea and sometimes resulting in irregular astigmatism or loss of best corrected visual acuity.

We propose lifting the corneal flap or cap when it is less than five months after the initial surgery. We have developed a corneal elevating instrument to atraumatically lift the edge of the flap or cap prior to using the above described Kritzinger/Updegraff LASIK corneal surface marker and irrigating cannula. This corneal elevator will be used to expose the corneal edge and a Colibri forceps can be used to peel back the overlying cap or flap. After the desired ablation is obtained, the flow tectonic repositioning of the corneal cap as described above is then used to return it to its correct anatomic position.

Figure 2:
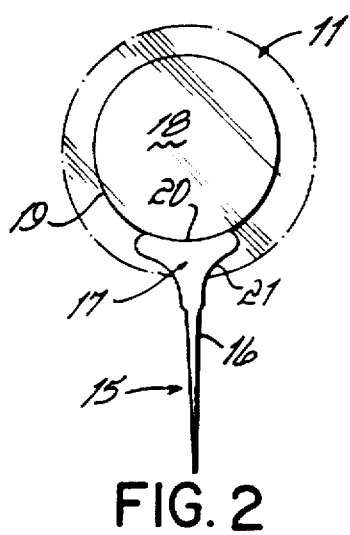
FIG. 2 illustrates a top view of the elevating instrument of this invention engaging a keratectomy edge on the corneal surface prior to lifting a corneal flap or cap.
Figure 3:
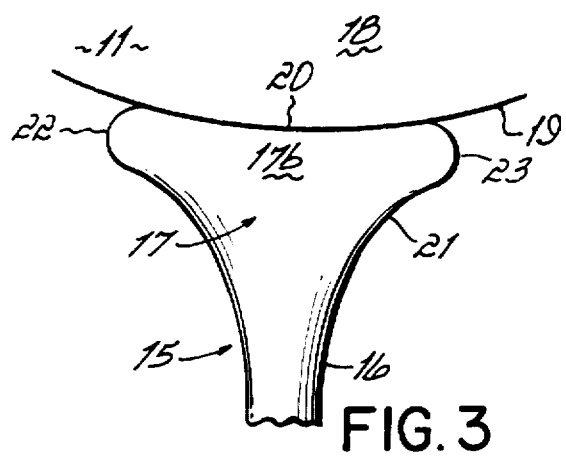
FIG. 3 illustrates an enlarged view of the region of FIG. 2 where the bottom portion of the elevating instrument engages and conforms to the keratectomy edge of the corneal surface.

With particular reference to the accompanying drawing FIGS. 1, 2 and 3, the corneal cap or flap elevating instrument of the present invention is shown generally at 15.

More particularly, FIG. 1 illustrates a side view of the elevating instrument 15 for use in atraumatically lifting a corneal cap or flap during corneal lamellar surgery. The instrument 15 has a stem or handle 16 which is angularly disposed, i.e., about 90°, with respect to the elevator head 17 to facilitate lifting in a preferred manner. The elevator head 17 is a curved blade having a vertical curvature whereby only the heel 17a and toe 17b engage the corneal epithelial surface 18. Further, toe 17b of instrument 15 engages the edge 19 of the keratectomy incision that was made by the surgeon and forces the edge 19 upward exposing the underlying surface for corrective ablation. Thus, the elevator head 17 has an incline convex top face 24 extending vertically away from a concave arcuate edge 20 which conforms to the edge 19 of the keratectomy. The heel 17a and toe 17b sections of head 17 have a bottom surface 17c which is concave in the preferred form so that only the heel and toe sections engage the corneal surface atraumatically.

Referring particularly to FIG. 2 which illustrates a top view of the present invention, instrument 15 engages the keratectomy edge 19 with elevator head 17. Keratectomy edge 19 circumferentially outlines a corneal flap or cap which is approximately 7 mm to 8 mm in diameter. The arcuate convex edge 20 atraumatically engages corneal keratectomy edge 19 where an initial incision has been made by the surgeon and atraumatically lifts corneal edge 19 to expose the underlying surface to be surgically altered or reshaped.

FIG. 3 illustrates an enlarged section of FIG. 2, and shows the arcuate edge 20 having a blunt or dull beveled portion 21. The beveled portion 21 aids in atraumatically lifting the corneal edge to expose the underlying surface. The edge 20 also has rounded ends 22 and 23. These prevent the tearing or other unintentional destruction of the corneal cap or flap when the edge 19 is engaged and lifted in order for the cap to be grasped and peeled by Colibri forceps prior to corrective ablation. In a preferred form, the dull and beveled portion 21 of arcuate edge 20 is gradually sloped to conform to keratectomy edge 19 and is approximately 3 mm to 4 mm in length. Thus, the elevator 17 can be gently swept across the corneal surface and will help the surgeon engage at the edge of where the initial incision was made temporally. The gentle sweeping will facilitate the lifting of the corneal flap or cap without tearing or causing distortion.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

We claim:

1. An elevating instrument for use in atraumatically lifting a corneal cap or flap during corneal lamellar surgery comprising a handle, and an elevator head at one end of said handle, said head having a concave leading edge with an inclined top face extending vertically upward away from said edge and a concave bottom surface for atraumatically engaging the corneal surface, said head adapts for insertion into a corneal cap or flap incision with said concave leading edge and inclined top face exposing a corneal edge for lifting the cap or flap.

2. The instrument of claim 1 wherein said elevator head is angularly disposed with respect to said handle to facilitate lifting the cap or flap.

3. The instrument of claim 2 wherein said elevator head is disposed at about 90° with respect to said handle.

4. The instrument of claim 1 wherein said top face is convex.

5. The instrument of claim 1 with said head having a heel section and a toe section, said handle connected to said heel section, said toe section forming said leading edge and inclined top face, said bottom surface being concave between said heel and toe sections.

6. The instrument of claim 5 wherein said bottom surface is configured for engagement of only said heel and toe sections of said head with the corneal surface.

7. The instrument of claim 1 wherein said concave leading edge is blunt to prevent tearing of the corneal edge.

8. The instrument of claim 7 wherein said arcuate edge is beveled and has rounded ends.

9. The instrument of claim 7 wherein said concave ading edge is sloped and is approximately 3 mm to 4 mm in length.

10. An elevating instrument for use in atraumatically lifting a corneal cap or flap during corneal lamellar surgery comprising a handle, and an elevator head angularly disposed at one end of said handle, said head having a concave leading edge with an inclined convex top face extending vertically upward away from said edge and a concavl bottom surface for atraumatically engaging the corneal surface, said head adapts for insertion into a corneal cap or flap incision with said concave leading edge and inclined top face exposing a corneal edge for lifting the cap or flap, said head having a heel section and a toe section, said handle connected to said heel section, said toe section forming said leading edge and inclined top face, said bottom surface being concave between said heel and toe sections.

11. The elevating instrument of claim 10 wherein said concave leading edge is beveled and has rounded ends.

12. The elevating instrument of claim 10 wherein said bottom surface is configured so that only said heel and toe sections of said head engage the corneal surface.

13. A method of atraumatically lifting a corneal flap or cap during corneal lamellar surgery comprising providing a corneal elevating instrument having a handle and an elevator head with a concave leading edge and an inclined top face extending vertically upward away from said edge and having a concave bottom surface for atraumatically engaging the corneal surface, placing said instrument at the edge of a corneal cap or flap incision, exposing said corneal flap or cap edge by inserting the elevator edge into the incision and atraumatically lifting said edge on said inclined top face, and peeling back said edge to provide said cap or flap.

14. The method according to claim 13 by placing said elevating instrument at the incision edge for lifting said corneal flap or cap in the temporal region of the corneal surface.

15. The method according to claim 13 wherein a forceps is used for peeling back said corneal flap or cap.

* * * * *